United States Patent
Scirica et al.

(10) Patent No.: US 9,039,736 B2
(45) Date of Patent: May 26, 2015

(54) SURGICAL STAPLING DEVICE WITH DISSECTING TIP

(75) Inventors: Paul A. Scirica, Huntington, CT (US); Todd L. Demmy, East Amherst, NY (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 1609 days.

(21) Appl. No.: 12/036,828

(22) Filed: Feb. 25, 2008

(65) Prior Publication Data

US 2008/0217375 A1 Sep. 11, 2008

Related U.S. Application Data

(60) Continuation of application No. 11/784,115, filed on Apr. 5, 2007, now Pat. No. 8,066,166, which is a continuation of application No. 11/030,527, filed on Jan. 6, 2005, now abandoned, which is a division of application No. 10/764,103, filed on Jan. 23, 2004.

(60) Provisional application No. 60/466,378, filed on Apr. 29, 2003.

(51) Int. Cl.
*A61B 17/068* (2006.01)
*A61B 17/072* (2006.01)
*A61B 17/32* (2006.01)

(52) U.S. Cl.
CPC .......... *A61B 17/07207* (2013.01); *A61B 17/068* (2013.01); *A61B 2017/07214* (2013.01); *A61B 2017/07271* (2013.01); *A61B 2017/320044* (2013.01)

(58) Field of Classification Search
CPC .......... A61B 17/07207; A61B 17/072; A61B 17/068; A61B 2017/07214; A61B 2017/0725; A61B 2017/07257; A61B 2017/07271
USPC .................... 227/175.1, 176.1, 179.1, 180.1; 606/142, 190, 205, 207, 211
See application file for complete search history.

(56) References Cited

U.S. PATENT DOCUMENTS

| | | | |
|---|---|---|---|
| 2,887,111 A * | 5/1959 | Leyro Diaz | 606/148 |
| 3,079,606 A | 3/1963 | Bobrov et al. | |
| 3,490,675 A | 1/1970 | Green et al. | |
| 4,429,695 A | 2/1984 | Green | |
| 4,505,414 A | 3/1985 | Filipi | |
| 4,589,413 A | 5/1986 | Malyshev et al. | |
| 4,602,634 A | 7/1986 | Barkley | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |

(Continued)

FOREIGN PATENT DOCUMENTS

| | | |
|---|---|---|
| DE | 2744824 | 2/1980 |
| DE | 2903159 | 7/1980 |

(Continued)

*Primary Examiner* — Ryan Severson

(57) ABSTRACT

A dissecting tip is provided for use with a surgical stapler or instrument. In one embodiment, the dissecting tip is secured to the end effector of the surgical instrument, e.g., to the cartridge assembly. The dissecting tip extends distally from the end effector and is configured to dissect or separate target tissue from certain tissue, e.g., adherent, connective, joined or other tissue.

12 Claims, 20 Drawing Sheets

(56) References Cited

U.S. PATENT DOCUMENTS

| | | |
|---|---|---|
| 4,703,887 A | 11/1987 | Clanton et al. |
| 4,728,020 A | 3/1988 | Green et al. |
| 4,784,137 A | 11/1988 | Kulik et al. |
| 4,815,465 A | 3/1989 | Alvarado |
| 4,863,088 A | 9/1989 | Redmond et al. |
| 4,892,244 A | 1/1990 | Fox et al. |
| 4,991,764 A | 2/1991 | Mericle |
| 5,040,715 A | 8/1991 | Breen et al. |
| 5,065,929 A | 11/1991 | Schulze et al. |
| 5,074,454 A | 12/1991 | Peters |
| 5,083,695 A | 1/1992 | Foslien et al. |
| 5,108,403 A | 4/1992 | Stern |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,633 A | 10/1992 | Smith |
| 5,170,925 A | 12/1992 | Madden et al. |
| 5,217,460 A | 6/1993 | Knoepfler |
| 5,219,354 A | 6/1993 | Choudhury et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,332,142 A | 7/1994 | Robinson et al. |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,415,334 A | 5/1995 | Williamson, IV et al. |
| 5,415,335 A | 5/1995 | Knodell, Jr. |
| 5,417,361 A | 5/1995 | Williamson, IV |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,464,300 A | 11/1995 | Crainich |
| 5,465,895 A | 11/1995 | Knodel |
| 5,467,911 A | 11/1995 | Tsuruta et al. |
| 5,470,007 A | 11/1995 | Plyley et al. |
| 5,470,010 A | 11/1995 | Rothfuss et al. |
| 5,474,566 A | 12/1995 | Alesi et al. |
| 5,476,206 A * | 12/1995 | Green et al. ............... 227/176.1 |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,937 A | 7/1996 | Boiarski et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A * | 10/1996 | Knodel et al. ............. 227/175.1 |
| 5,562,682 A | 10/1996 | Oberlin et al. |
| 5,564,615 A | 10/1996 | Bishop et al. |
| 5,573,543 A | 11/1996 | Akopov et al. |
| 5,577,654 A | 11/1996 | Bishop |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,649,957 A | 7/1997 | Levin |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,097 A | 9/1997 | Baker et al. |
| 5,665,100 A | 9/1997 | Yoon |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,982 A | 10/1997 | Schulze et al. |
| 5,690,269 A | 11/1997 | Bolanos et al. |
| 5,690,653 A | 11/1997 | Richardson et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,099 A | 6/1998 | Gravener |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,897,562 A | 4/1999 | Botanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,941,442 A | 8/1999 | Geiste et al. |
| 5,954,259 A | 9/1999 | Viola et al. |
| 6,001,120 A | 12/1999 | Levin |
| 6,004,335 A | 12/1999 | Vaitekunas et al. |
| 6,010,054 A | 1/2000 | Johnson et al. |
| 6,013,028 A | 1/2000 | Jho et al. |
| 6,032,849 A | 3/2000 | Mastri et al. |

(56) References Cited

U.S. PATENT DOCUMENTS

| | | | |
|---|---|---|---|
| 6,036,714 | A | 3/2000 | Chin |
| 6,079,606 | A | 6/2000 | Milliman et al. |
| 6,099,537 | A | 8/2000 | Sugai et al. |
| 6,109,500 | A | 8/2000 | Au et al. |
| 6,197,017 | B1 | 3/2001 | Brock et al. |
| 6,202,917 | B1 | 3/2001 | Weaver et al. |
| 6,241,139 | B1 | 6/2001 | Milliman et al. |
| 6,241,740 | B1 | 6/2001 | Davis et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,269,977 | B1 | 8/2001 | Moore |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,439,446 | B1 | 8/2002 | Perry et al. |
| 6,443,973 | B1 | 9/2002 | Whitman |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,656,193 | B2 | 12/2003 | Grant et al. |
| 6,679,895 | B1 | 1/2004 | Sancoff et al. |
| 6,698,643 | B2 | 3/2004 | Whitman |
| 6,722,552 | B2 | 4/2004 | Fenton, Jr. |
| 6,755,815 | B2 | 6/2004 | Schultz |
| 6,761,725 | B1 | 7/2004 | Grayzel et al. |
| 7,131,978 | B2 | 11/2006 | Sancoff et al. |
| 7,308,998 | B2 | 12/2007 | Mastri et al. |
| 2001/0034535 | A1 | 10/2001 | Schultz |
| 2003/0065351 | A1 | 4/2003 | Hess et al. |
| 2004/0019355 | A1 | 1/2004 | Mehdizadeh |

FOREIGN PATENT DOCUMENTS

| | | |
|---|---|---|
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0537572 | 4/1993 |
| EP | 0539762 | 5/1993 |
| EP | 0545029 | 6/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 216559 | 4/1986 |
| RU | 728848 | 5/1977 |
| RU | 659146 | 4/1979 |
| RU | 980703 | 12/1982 |
| RU | 990220 | 1/1983 |
| WO | WO89/10094 | 11/1989 |
| WO | WO92/10976 | 7/1992 |
| WO | WO93/08754 | 5/1993 |
| WO | WO83/02247 | 7/1993 |
| WO | WO93/14706 | 8/1993 |

\* cited by examiner

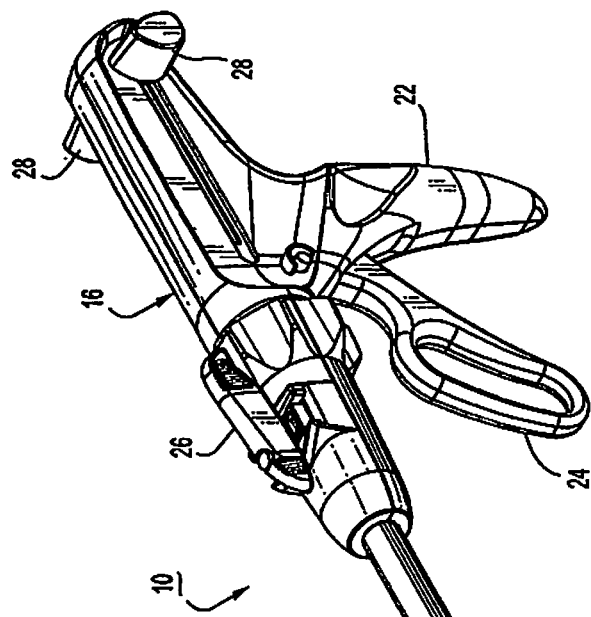
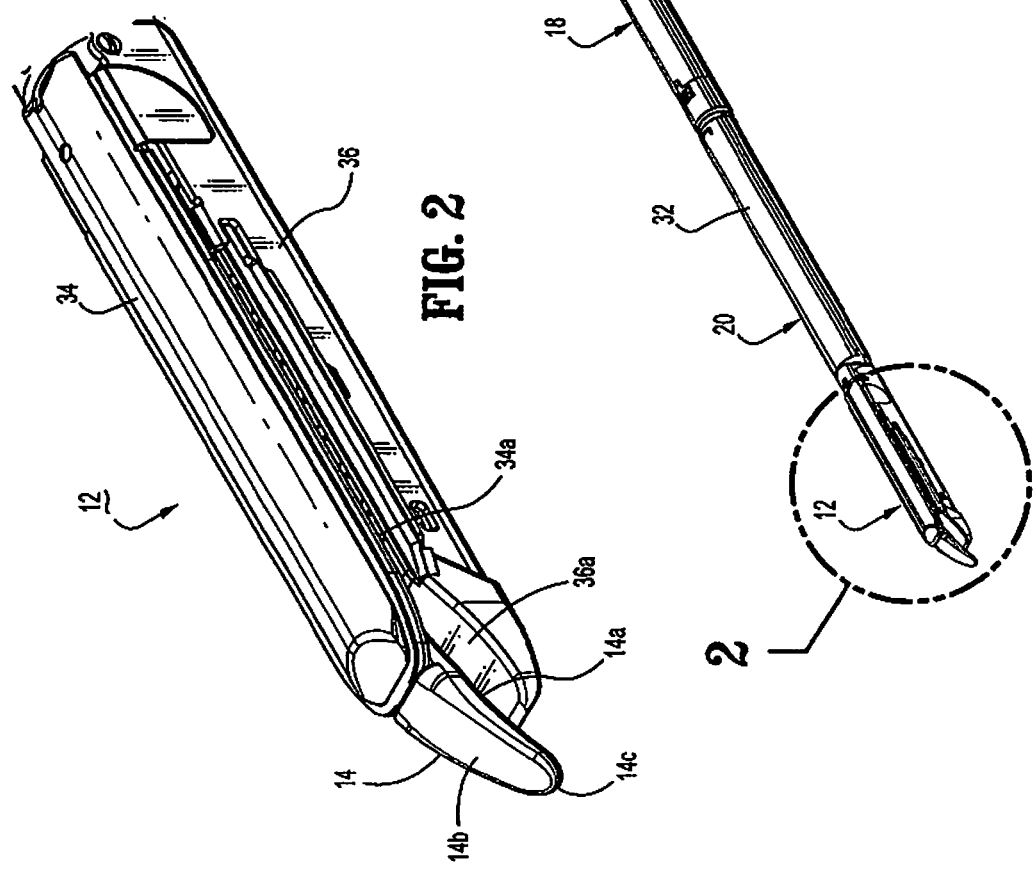

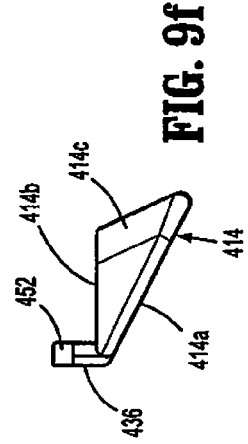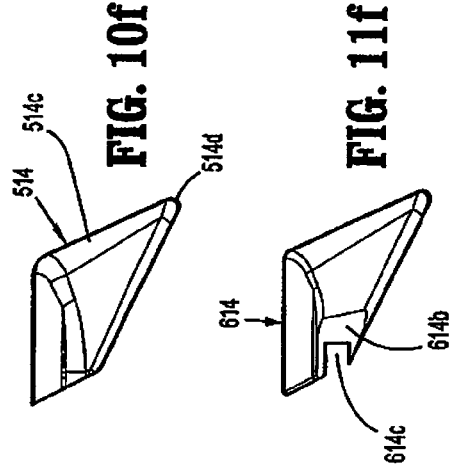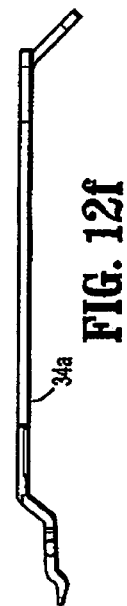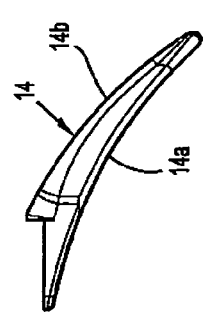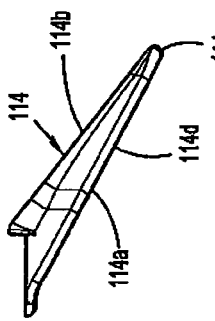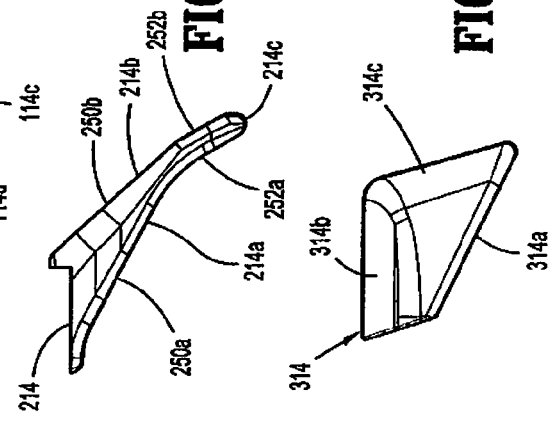

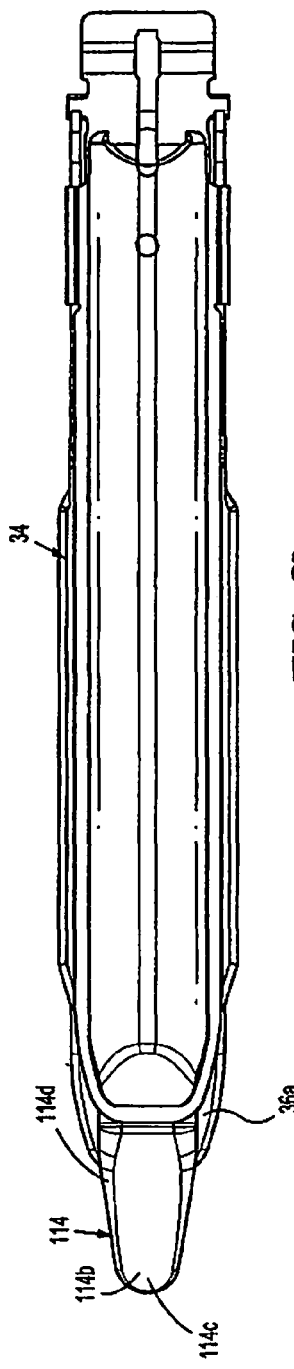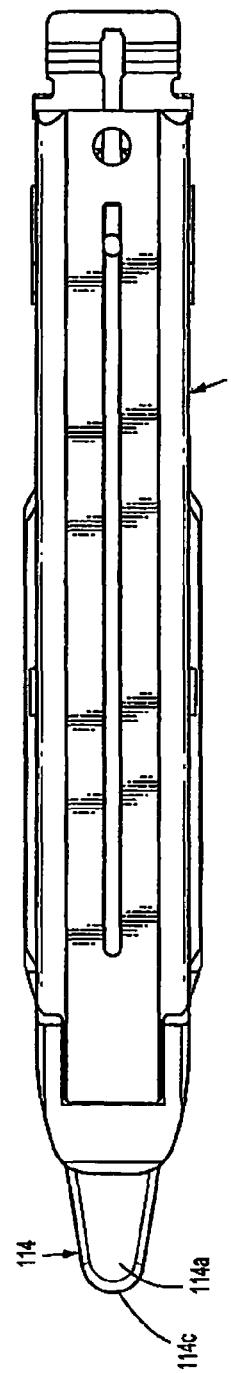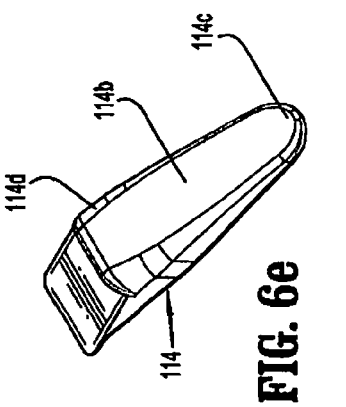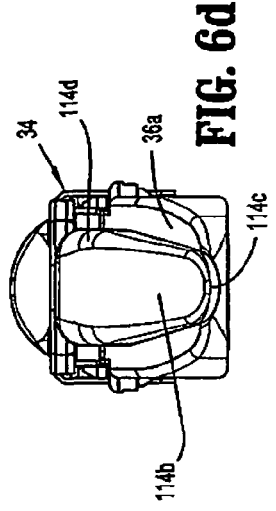
FIG. 6b
FIG. 6c
FIG. 6d
FIG. 6e

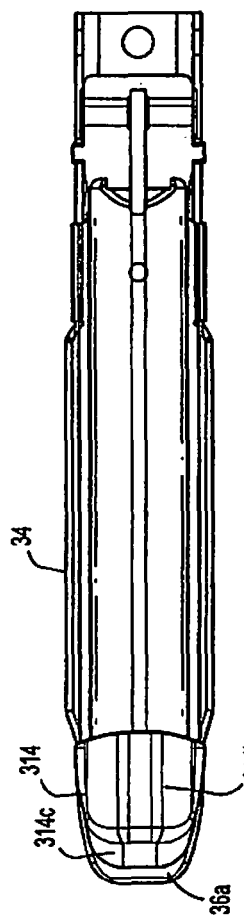
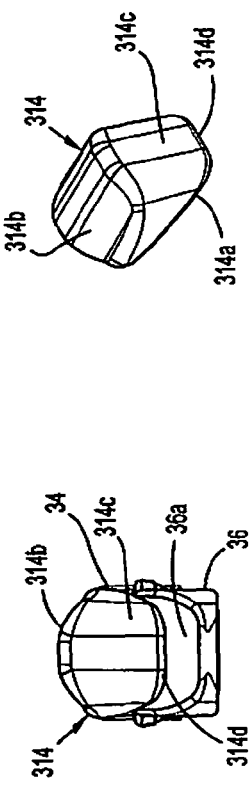
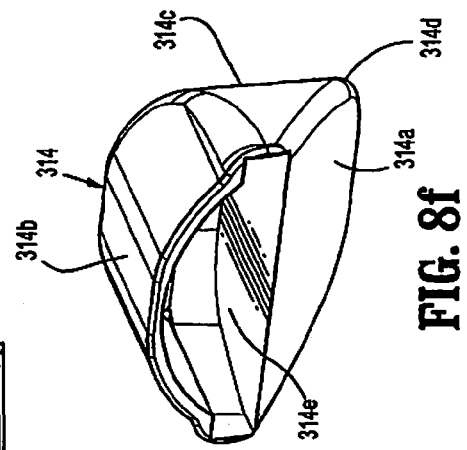
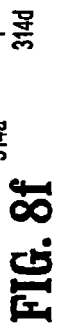
FIG. 8b
FIG. 8c
FIG. 8d
FIG. 8e
FIG. 8f

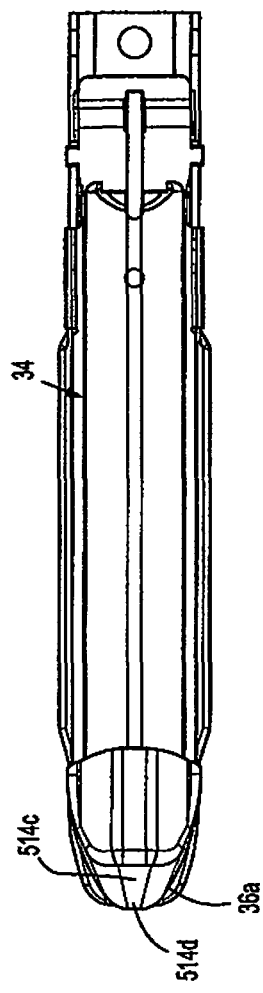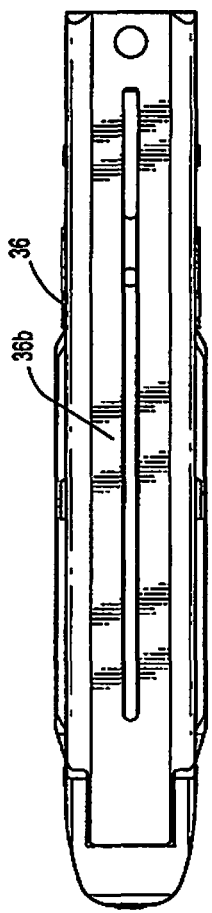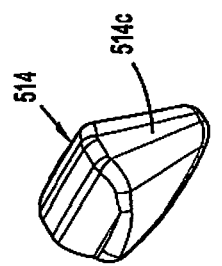
FIG. 10b
FIG. 10c
FIG. 10d
FIG. 10e

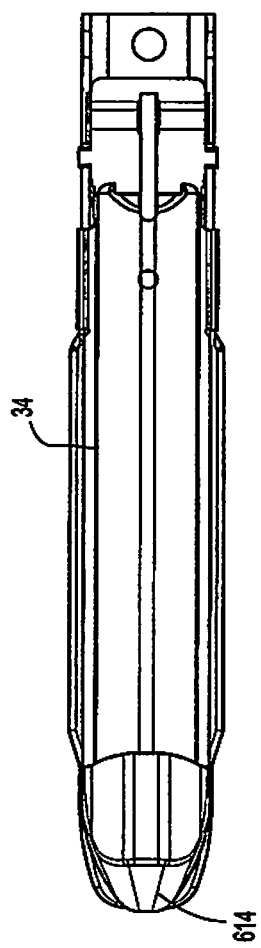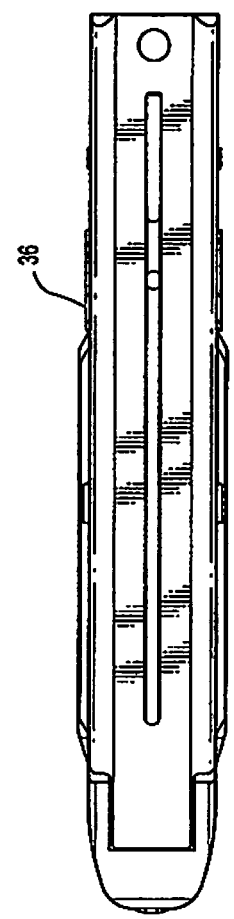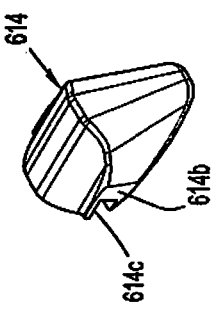
FIG. 11b
FIG. 11c
FIG. 11d
FIG. 11e a # SURGICAL STAPLING DEVICE WITH DISSECTING TIP This application is a continuation application of U.S. application Ser. No. 11/784,115, filed Apr. 5, 2007, which is a continuation of U.S. application Ser. No. 11/030,527, filed Jan. 6, 2005, which is a divisional of U.S. application Ser. No. 10/764,103, filed Jan. 23, 2004, which claims priority from U.S. Provisional Application No. 60/466,378 filed Apr. 29, 2003. Each of which are incorporated herein in their entirety by reference.

BACKGROUND

1. Technical Field

This application relates to a surgical stapling device. More particularly, this application relates to a surgical stapling device having an improved tip construction for accessing and/or separating tissue.

2. Background of Related Art

Surgical staple or fastener applying devices for joining tissue are well known. Typically, such devices include opposing jaw structure for grasping and clamping selected tissue, wherein one of the jaws of the opposing jaw structure includes a cartridge which houses a plurality of staples or fasteners. In some instruments, a knife is provided to cut tissue which has been joined by the staples or fasteners.

Linear surgical stapling devices, for example, include two elongated members which are relatively moveable to capture or clamp tissue. Typically one of the members includes a cartridge which houses a plurality of staples arranged in two or more linear rows and the other member includes an anvil having a plurality of staple forming pockets for receiving and forming the legs of the staples. A knife is movably positioned between the linear rows of staples such that when the stapling device is positioned about tissue and actuated, the tissue is joined and/or simultaneously or nearly simultaneously cut.

Linear surgical stapling devices are commonly used during surgical procedures to simultaneously seal and cut target tissue, e.g., vasculature, organs, etc. It is not uncommon during such procedures that certain tissue, e.g., vasculature or other adherent, connective, joined or other tissue, adheres or is joined to the target tissue and must first be separated from the target tissue before the procedure can continue. Currently, a surgical device separate from the stapling device is used to dissect or separate the certain tissue from the target tissue before the target tissue and/or the adherent certain tissue is operated upon. Also, it is a known practice to attach a guide or carrier tube to the distal end of the anvil and to use a separate instrument to pass the tube around the target tissue or structure. The tube is also used to move the back wall of the target tissue into the jaws of the stapling device. The tube is removed after the staple is in proper position and then the stapler is fired. These procedures require extra steps and devices and can be time consuming and expensive especially during endoscopic procedures.

Accordingly, a continuing need exists in the art for a device which can be used not only to join and cut tissue but also to separate or dissect certain, e.g., adherent, tissue from target tissue.

SUMMARY

In accordance with the present disclosure, a dissecting tip is provided for use with a surgical stapling device and, especially, a linear surgical stapling device, including an end effector having an anvil assembly and a cartridge assembly. The dissecting tip is supported on the end effector, preferably, on the distal end of the anvil assembly. The dissecting tip can instead or also be supported on the distal end of the cartridge assembly. The dissecting tip can be positioned to extend distally from the anvil assembly and includes a body having an outer surface, an inner surface and a distal tip. The body may assume a variety of configurations. For example, the body may include inner and/or outer surfaces which are curved along the longitudinal and/or transverse axis of the anvil assembly and extend downwardly towards the cartridge assembly. In another preferred embodiment, the inner and/or outer surfaces are substantially flat. In yet another preferred embodiment, the inner and/or outer surfaces include a pair of flat sections interconnected by a curved transition section. Preferably, the width of the dissecting tip decreases from the proximal end of the dissecting tip to the distal end of the dissecting tip. The distal tip of the dissecting tip is preferably rounded and blunt to prevent snagging, pulling and/or cutting of tissue.

The dissecting tip functions to dissect or separate target tissue and certain tissue. As discussed above, "certain tissue" includes adherent, connective, joined or other tissue. This is preferably accomplished by passing or pressing the outer surface of dissecting tip against the target tissue and pushing the distal tip of the dissecting tip behind the certain tissue such that the certain tissue is positioned adjacent the inner surface of the dissecting tip. Preferably, the dissecting tip is located and dimensioned to permit access through a trocar cannula assembly sized to receive the surgical stapling instrument without the dissecting tip.

BRIEF DESCRIPTION OF THE DRAWINGS

Various preferred embodiments of the presently disclosed dissecting tip are described herein with reference to the drawings, wherein:

FIG. 1 is a side top perspective view of a surgical stapling device including one preferred embodiment of the presently disclosed dissecting tip attached to the end effector thereof;

FIG. 2 is an enlarged view of the indicated area of detail shown in FIG. 1;

FIG. 5b is a bottom view of the dissecting tip and end effector shown in FIG. 5a;

FIG. 5e is a side view of the dissecting tip shown in FIG. 5d;

FIG. 6b is a top view of the dissecting tip and end effector of the surgical stapling device shown in FIG. 6;

FIG. 6c is a bottom view of the dissecting tip and end effector shown in FIG. 6b;

FIG. 6d is a front view of the dissecting tip and end effector shown in FIG. 6c;

FIG. 6e is a side top perspective view from the front of the presently disclosed dissecting tip shown in FIG. 6;

FIG. 6f is a side view of the dissecting tip shown in FIG. 6e;

FIG. 7f is a side view of the dissecting tip shown in FIG. 7e;

FIG. 8b is a top view of the dissecting tip and end effector of the surgical stapling device shown in FIG. 8;

FIG. 8c is a bottom view of the dissecting tip and end effector shown in FIG. 8b;

FIG. 8d is a front view of the dissecting tip and end effector shown in FIG. 8c;

FIG. 8e is a side perspective view from the front of the presently disclosed dissecting tip shown in FIG. 8;

FIG. 8f is a side perspective view from the rear of the dissecting tip shown in FIG. 8e;

FIG. 8g is a side view of the dissecting tip shown in FIG. 8e;

FIG. 9f is a side view of the dissecting tip shown in FIG. 9e;

FIG. 10b is a top view of the dissecting tip and end effector of the surgical stapling device shown in FIG. 10;

FIG. 10c is a bottom view of the dissecting tip and end effector shown in FIG. 10b;

FIG. 10d is a front view of the dissecting tip and end effector shown in FIG. 10c;

FIG. 10e is a side perspective view from the front of the presently disclosed dissecting tip shown in FIG. 10;

FIG. 10f is a side view of the dissecting tip shown in FIG. 10e;

FIG. 11b is a top view of the dissecting tip and end effector of the surgical stapling device shown in FIG. 11;

FIG. 11c is a bottom view of the dissecting tip and end effector shown in FIG. 11b;

FIG. 11d is a front view of the dissecting tip and end effector shown in FIG. 11c;

FIG. 11e is a side perspective view from the front of the presently disclosed dissecting tip shown in FIG. 11;

FIG. 11f is a side view of the dissecting tip shown in FIG. 11e;

FIG. 12f is a side view of the dissecting tip shown in FIG. 12e; and

DETAILED DESCRIPTION OF PREFERRED EMBODIMENTS

Figure 3:
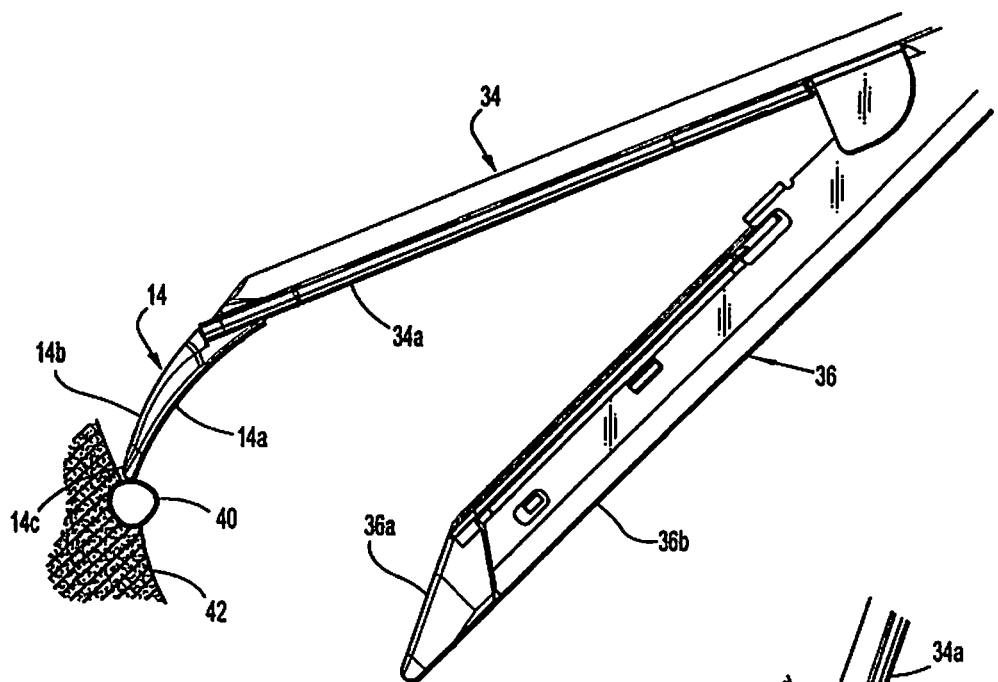
FIG. 3 is a side view of the end effector with portions broken away and of the dissecting tip of the surgical stapling device shown in FIG. 1 with the end effector in the open position adjacent target tissue and certain tissue which is adhered to the target tissue.

Preferred embodiments of the presently disclosed surgical stapling device with dissecting tip will now be described in detail with reference to the drawings wherein like reference numerals designate identical or corresponding elements in each of the several views.

In the description that follows, the term "proximal", as is traditional, will refer to the end of the stapling device closest the operator and the term "distal" will refer to the end of the stapling device furthest from the operator.

FIG. 1 illustrates a linear surgical stapling device shown generally as 10 including an end effector 12 having one preferred embodiment of the presently disclosed dissecting tip, here generally designated 14, supported thereon. Stapling device 10 also includes a handle assembly 16 and an endoscopic portion 18. End effector 12 forms part of a disposable loading unit or single use loading unit (SULU) 20. With the exception of dissecting tip 14, the remaining components of surgical stapling device 10 are substantially as described in U.S. Pat. No. 5,865,361 ("'361 patent"), U.S. Pat. Nos. 6,079, 606, 6,241,139, 6,330,965 and 6,669,073 which are incorporated herein in their entirety by reference. It is contemplated that the presently disclosed embodiments of the dissecting tip may be used in association with other known linear stapling devices of both endoscopic and open construction. These devices include articulating and non-articulating devices as well as reusable and non-reusable devices. Examples of such devices are disclosed in U.S. Pat. Nos. 6,202,914, 6,250,532, 6,109,500, 6,032,849, 5,584,425, 5,540,375, 5,554,169, 5,507,426, 5,482,197, which are also incorporated herein in their entirety by reference. In light of the comments above, only the preferred embodiments of the dissecting tips disclosed herein will be discussed in detail in this application.

FIGS. 1-5c illustrate one preferred embodiment of the presently disclosed dissecting tip in combination with a surgical stapling device 10. As discussed above, surgical stapling device 10 includes a handle assembly 16, an elongated body or endoscopic portion 18, and a SULU 20. Briefly, handle assembly 16 includes a stationary grip member 22, a pivotable trigger 24, an articulation lever 26, a rotation knob 27 and return knobs 28. SULU 20 is adapted to be releasably attached to elongated body portion 18 and includes a proximal body portion 32 and end effector 12. End effector 12 is pivotally attached to proximal body portion 32 to facilitate articulation of end effector 12 in relation to proximal body portion 32.

End effector 12 includes an anvil assembly 34 and a cartridge assembly 36 which houses a plurality of linear rows of staples. Anvil assembly 34 and cartridge assembly 36 are movable, here, pivotal in relation to each other between an open position and a clamped or approximated position. Pivotable trigger 24 is actuable through an actuation stroke or strokes to move anvil assembly 34 in relation to cartridge assembly 36 between the open position and the clamped position and to eject staples from cartridge assembly 36. The operation of each of these components is described in greater detail in the '361 patent and will not be discussed in further detail herein.

Dissecting tip 14 is secured to a distal end of the end effector 12. Alternately, dissecting tip may be integrally formed with end effector 12 or end effector 12 and dissecting tip 14 may be of monolithic construction. In one preferred embodiment, dissecting tip 14 is secured to a distal surface of anvil assembly 34 which is contiguous with a tissue contact surface 34a of anvil assembly 34. Dissecting tip 14 is preferably formed from a surgical grade metal or plastic and is attached to anvil assembly 34 using any known suitable fastening technique, e.g., adhesives, welding, soldering, brazing, pins, etc. Alternately, other known surgically approved materials may be used to construct dissecting tip 14. In this preferred embodiment, dissecting tip 14 includes a curved preferably smooth inner surface 14a, preferably also a curved, smooth outer surface 14b and a rounded preferably thin blunt tip 14c. The curved surface can be formed by any suitable radius. A one inch radius has been found suitable for certain applications. Curved inner surfaces may be formed by a plurality of curves, wherein each of the curves is defined by a radius of curvature. Smooth surfaces prevent dissecting tip 14 from snagging, pulling and/or cutting tissue. Inner surface 14a of dissecting tip 14 extends downwardly towards cartridge assembly 36 to a location beyond the distal end of cartridge assembly 36. By extending dissecting tip 14 beyond cartridge assembly 36, access to adherent tissue is improved and visualization of the tip to confirm proper position and that dissection of the adherent tissue is completed is permitted. The width of the dissecting tip 14 decreases from its proximal end to its distal end and at its greatest with is smaller than the width of cartridge assembly 36. Desirably there are substantially smooth blends or transitions from the dissecting tip to the portion(s) of the jaw structure to which the tip is secured or from which it extends. When anvil assembly 34 and cartridge assembly 36 are in the clamped or approximated position, dissecting tip 14 is spaced from a distal angled tissue guide surface 36a of cartridge assembly 36. Preferably, the space therebetween is at least the same, or preferably greater, e.g., two times greater, than the gap between the tissue contacting surfaces of the anvil and cartridge assemblies when they are approximated. However, there may be instances when it may be desired to have less space between the dissecting tip and the tissue guide surface of the cartridge, for example when it is desired to compress tissue there.

Figure 4A:
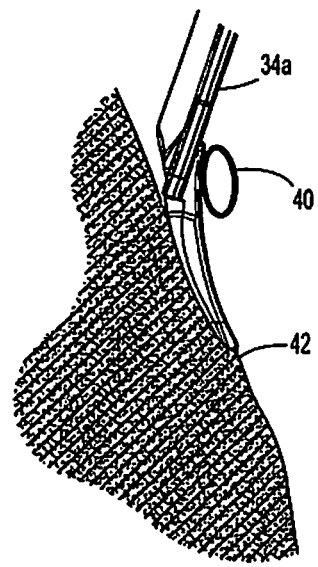
FIG. 4a is a side view of the anvil assembly and dissecting tip shown in FIG. 4 positioned fully between the certain tissue and the target tissue.
Figure 4:
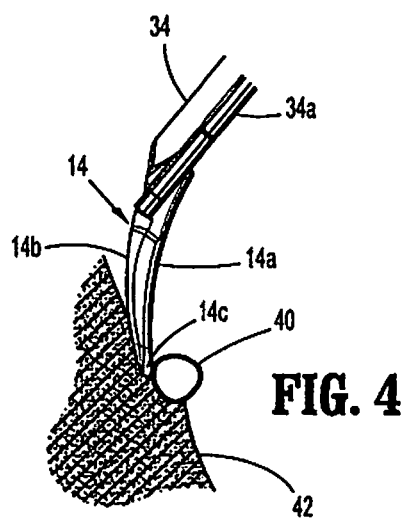
FIG. 4 is a side view of the anvil assembly shown in FIG. 3 with the dissecting tip positioned partially between the certain tissue and the target tissue.
Figure 5:
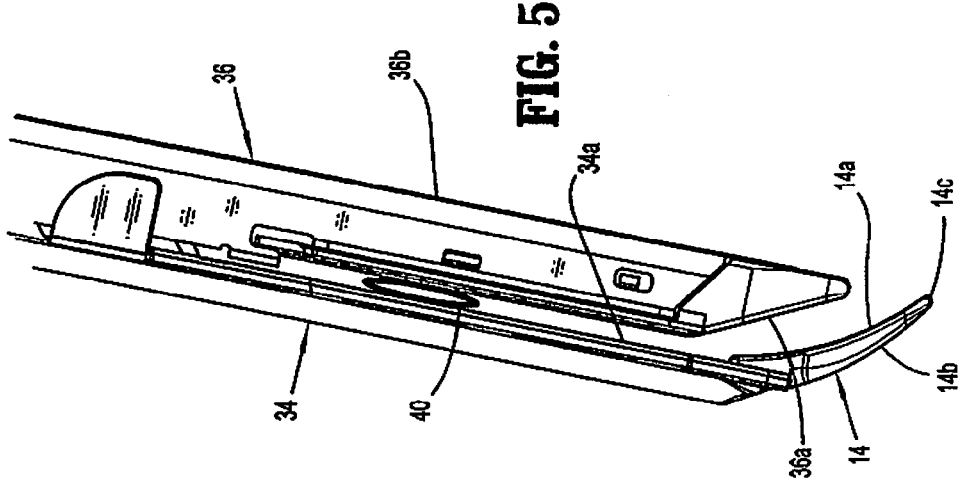
FIG. 5 is a side view of the dissecting tip and end effector shown in FIG. 4b with certain tissue positioned between a clamped anvil assembly and cartridge assembly.
Figure 4B:
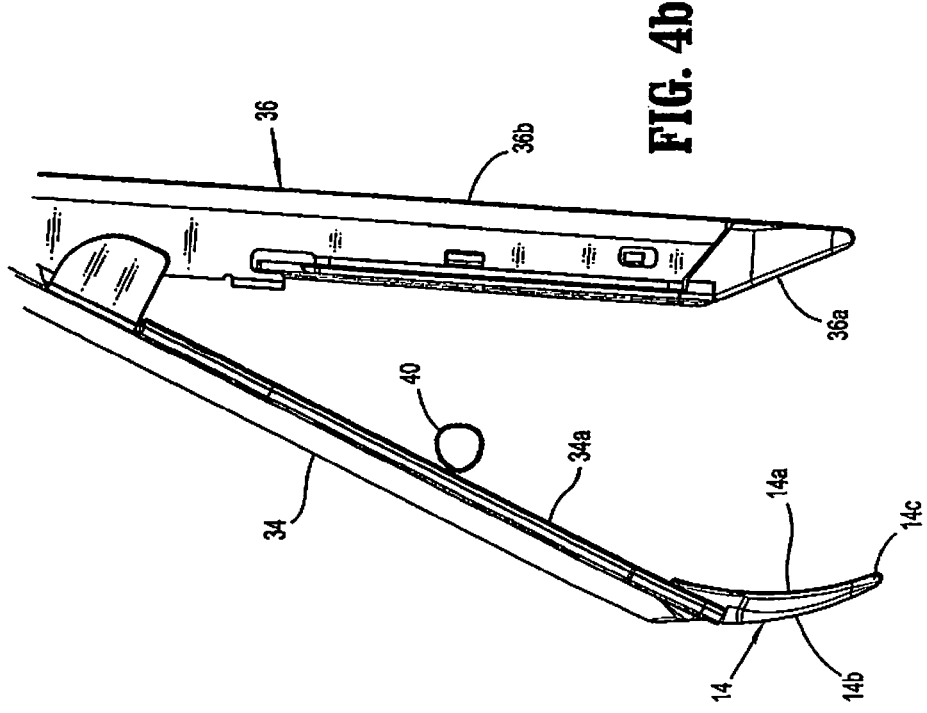
FIG. 4b is a side view of the dissecting tip and end effector shown in FIG. 3 with certain tissue positioned between an open anvil assembly and cartridge assembly.
Figure 5A:
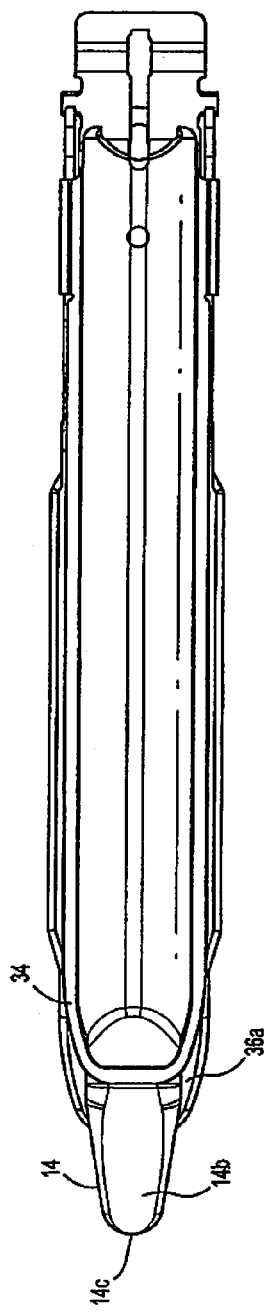
FIG. 5a is a top view of the dissecting tip and end effector of the surgical stapling device shown in FIG. 1.
Figure 5B:
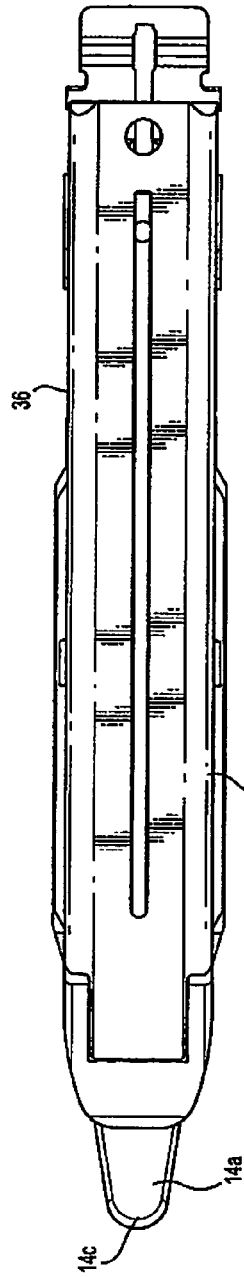
Figure 5D:
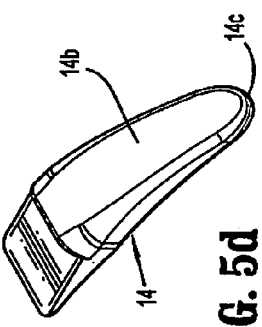
FIG. 5d is a side perspective view from the front of the presently disclosed dissecting tip dissector shown in FIG. 1.
Figure 5C:
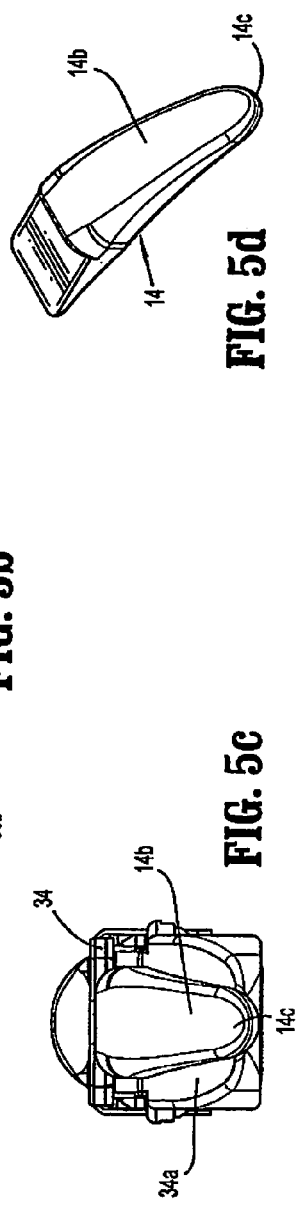
FIG. 5c is a front view of the dissecting tip and end effector shown in FIG. 5b.

Referring now to FIGS. 3-5, when surgical stapling device 10 is used to dissect certain tissue 40, e.g., blood or airway vessels, from target tissue 42, e.g., stomach, lung, etc., curved outer surface 14b of dissecting tip 14 can be pressed or passed against the target tissue 42 and slid behind certain tissue 40, e.g. adherent tissue, to separate and/or dissect tissue 40 from, for example, adherence with target tissue 42. Positioning of dissecting tip 14 behind certain tissue 40 is preferably accomplished with the anvil assembly 34 and the cartridge assembly 36 in the open position. Alternatively, the anvil and cartridge assemblies can be moved to the clamped position to provide extra stability to the end effector during dissection of tissue. Thereafter, either or both of certain tissue 40 and target tissue 42 can be independently joined and cut by clamping and actuating surgical stapling device 10.

It is noted that although not described in detail, end effector 12 preferably is adapted to access the surgical site through a trocar cannula assembly as is known in the art. To accomplish this, anvil assembly 34 and cartridge assembly 36 are maintained in a clamped position as elongated body portion 18 and end effector 12 are inserted through the cannula (not shown). As illustrated, preferably, dissecting tip 14 does not extend below a plane defined by a bottom surface 36b of cartridge assembly 36, nor does dissecting tip 14 extend outwardly beyond the sidewalls of cartridge assembly 36. The dissecting tip can be positioned above, preferably slightly above, the plane. As such, surgical stapling device 10 including dissecting tip 14 may be used with a trocar cannula assembly sized to receive a surgical stapling device not having a dissecting tip 14.

Figure 6:
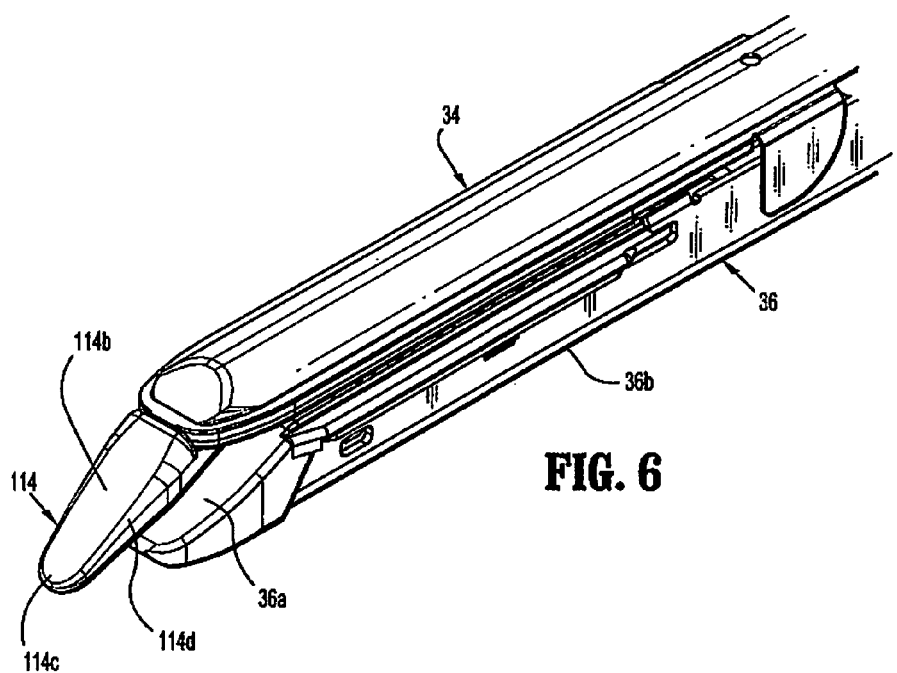
FIG. 6 is an enlarged top side perspective view from the front of the end effector of a surgical stapling device including another preferred embodiment of the presently disclosed dissecting tip.
Figure 6A:
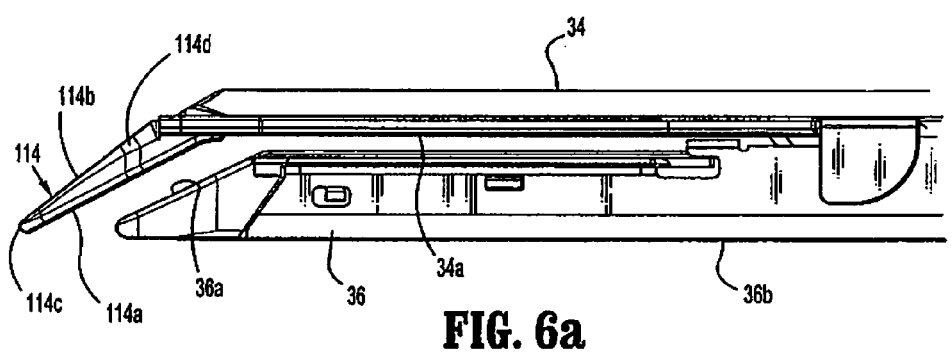
FIG. 6a is a side view of the dissecting tip and end effector shown in FIG. 6.

FIGS. 6-6e illustrate another preferred embodiment of the presently disclosed dissecting tip shown generally as 114. Dissecting tip 114 is secured to the distal end of end effector 12. Alternately, dissecting tip 114 can be monolithically or integrally formed with end effector 12. As discussed above, end effector 12 includes anvil assembly 34 and cartridge assembly 36. Dissecting tip 114 is secured to a distal surface or portion of anvil assembly 34 in the manner described above with respect to dissecting tip 14. Dissecting tip 114 is also constructed from a surgical grade metal or plastic and includes substantially flat inner and outer surfaces 114a and 114b and a rounded, blunt tip 114c. The use of other known surgically approved materials to construct dissecting tip 114 is envisioned. Other tip configurations may also be employed. The outer edges 114d of outer surface 114b are preferably rounded to prevent snagging, and/or cutting of tissue. Inner surface 114a of dissecting tip 114 is preferably substantially parallel to and spaced from tissue guide surface 36a of cartridge assembly 36 when anvil assembly 34 and cartridge assembly 36 are in the clamped position. Distal tip 114c of dissecting tip 114 extends distally beyond the distal end of cartridge assembly 36 and decreases in width from its proximal end to its distal end. The width of the proximal end of dissecting tip 114 is smaller than the width of cartridge assembly 36 and distal tip 114c preferably does not extend below a plane defined by a bottom surface 36b of cartridge assembly 36. As such, a surgical stapling device including dissecting tip 114 can be inserted through a trocar cannula assembly sized to receive the stapling device.

The use of dissecting tip 114 is substantially identical to that of dissecting tip 14 and will not be discussed in further detail herein.

Figure 7:
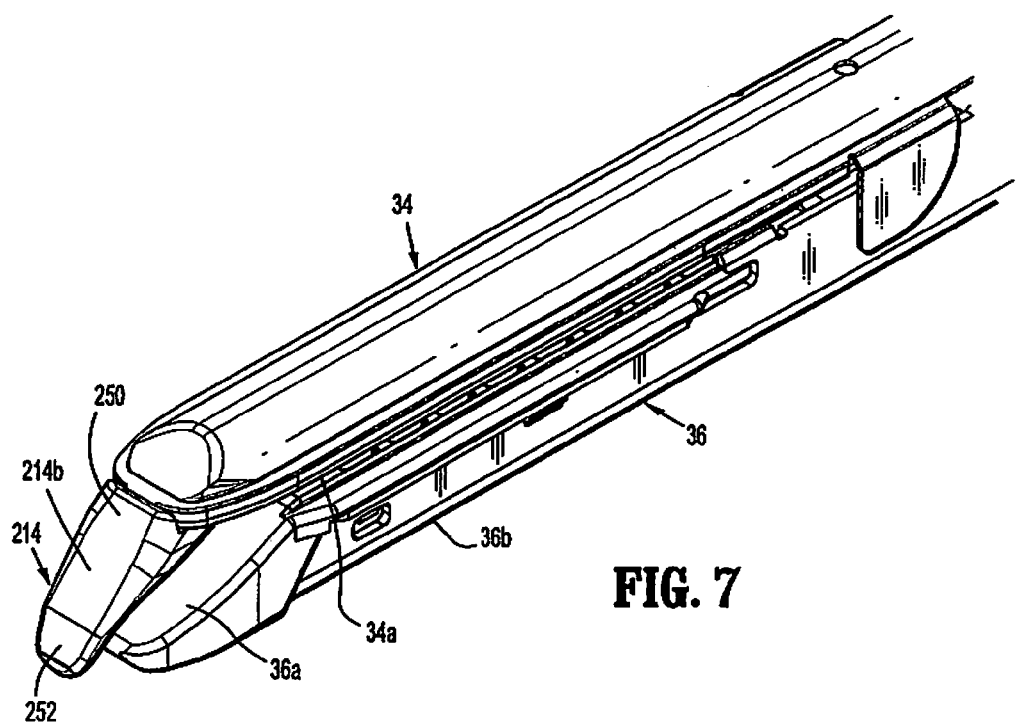
FIG. 7 is an enlarged side top perspective view from the front of the end effector of a surgical stapling device including another preferred embodiment of the presently disclosed dissecting tip.
Figure 7A:
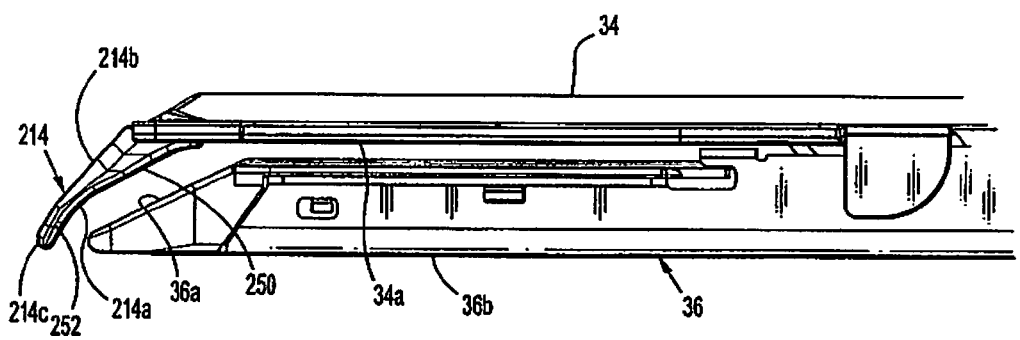
FIG. 7a is a side view of the dissecting tip and end effector shown in FIG. 7.
Figure 7B:
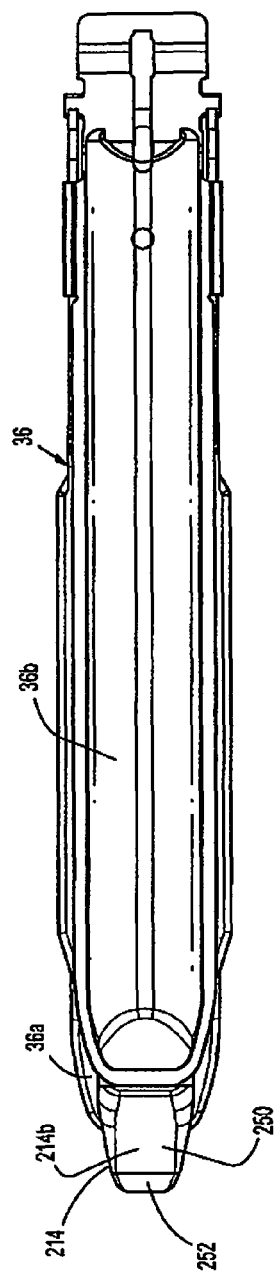
FIG. 7b is a top view of the dissecting tip and end effector of the surgical stapling device shown in FIG. 7.
Figure 7C:
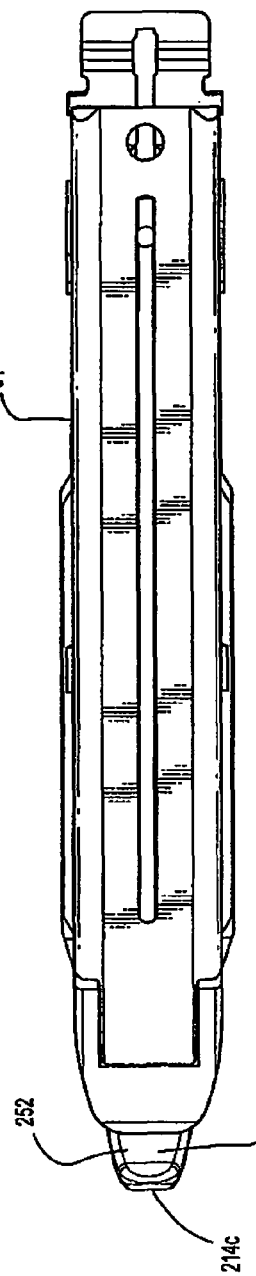
FIG. 7c is a bottom view of the dissecting tip and end effector shown in FIG. 7b.
Figure 7E:
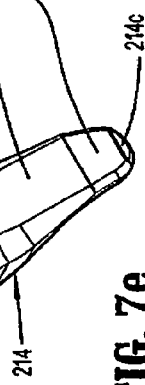
FIG. 7e is a side top perspective view from the front of the presently disclosed dissecting tip shown in FIG. 7.
Figure 7D:
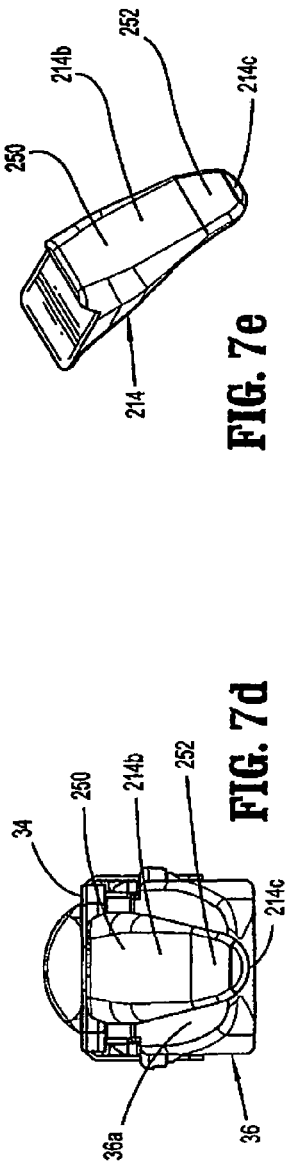
FIG. 7d is a front view of the dissecting tip and end effector shown in FIG. 7c.

FIGS. 7-7e illustrate another preferred embodiment of the presently disclosed dissecting tip shown generally as 214. Dissecting tip 214 is secured onto anvil assembly 34 of end effector 12 in the manner described above with respect to dissecting tip 14. Dissecting tip 214 is also constructed from a surgical grade metal or plastic. Alternatively, the use of other known materials of construction is envisioned.

Dissecting tip 214 includes inner and outer surfaces 214a and 214b and a blunt tip 214c. Inner and outer surfaces 214a and 214b preferably each have a substantially flat proximal portion 250a and 250b and a substantially flat distal portion 252a and 252b positioned at an angle to proximal portion 250. Preferably, proximal portion 250 and distal portion 252 along inner surface 214a define an angle θ (FIG. 7a) of between about 10° and about 90°, and most preferably about 30°. The transition between proximal portion 250a and distal portion 252a is smooth and rounded to prevent snagging, pulling and/or cutting of tissue. The outer surface of tip 214 can have other shapes, e.g., rounded as in FIGS. 1-5e. As discussed above with respect to dissecting tips 14 and 114, the width of dissecting tip 214 decreases from its proximal end to its distal end and at its greatest width is less than the width of cartridge assembly 36. The distal end of distal portion 252a includes a blunt tip 214c which preferably does not extend beyond a plane defined by a bottom surface 36b of cartridge assembly 36. The use of dissecting tip 214 is substantially identical to that of dissecting tip 14 and will not be discussed in further detail herein.

Figure 8:
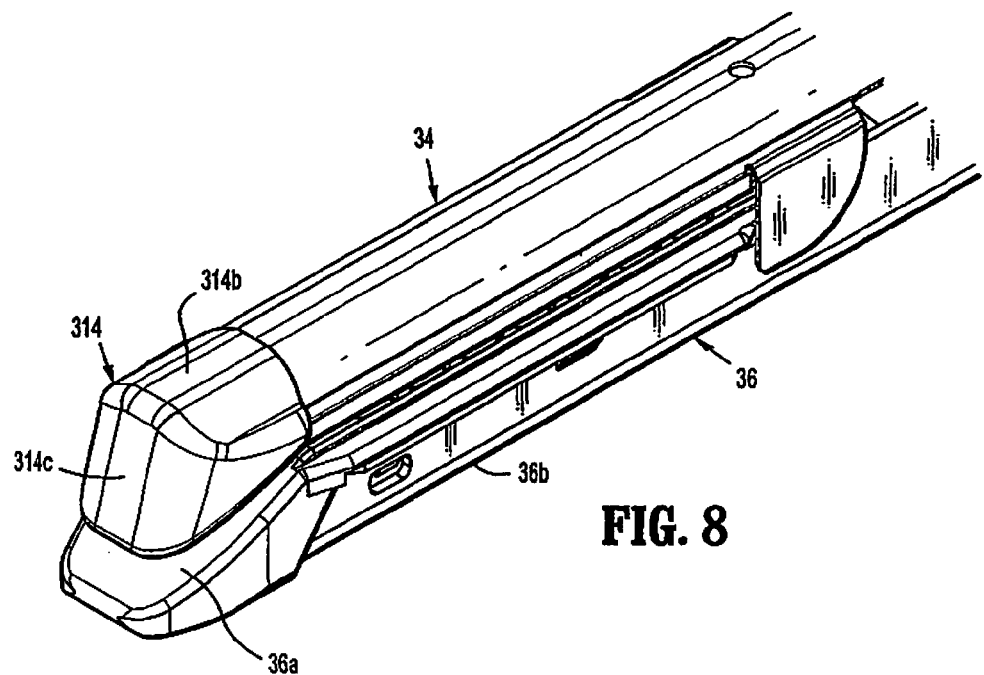
FIG. 8 is an enlarged side perspective view from the front of the end effector of a surgical stapling device including another preferred embodiment of the presently disclosed dissecting tip.
Figure 8A:
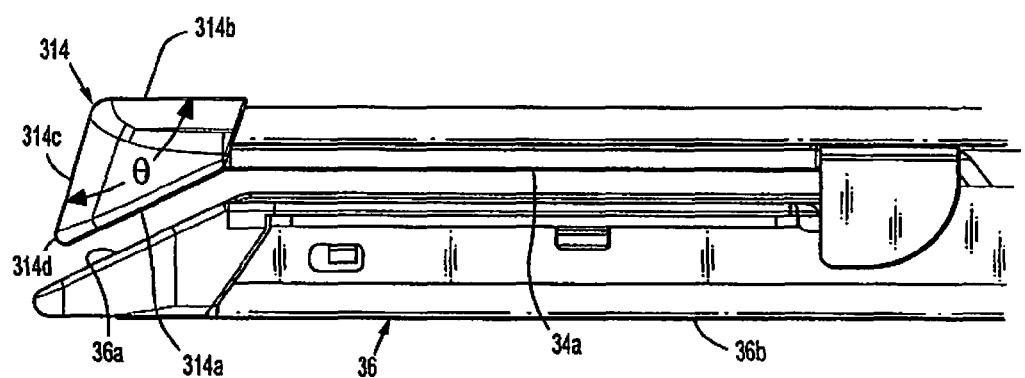
FIG. 8a is a side view of the dissecting tip and end effector shown in FIG. 8.

FIGS. 8-8e illustrate another preferred embodiment of the presently disclosed dissecting tip shown generally as 314. Dissecting tip 314 includes an inner surface 314a, a top surface 314b and a front surface 314c. Inner surface 314a is angled and is substantially parallel to distal angled tissue guide surface 36a of cartridge assembly 36. Top surface 314b is curved or concave along an axis transverse to a longitudinal axis of anvil assembly 34. Front surface 314c is angled downwardly towards cartridge assembly 36 and preferably defines an angle θ (FIG. 8a) of between about 95° and 135° with respect to the longitudinal axis of anvil assembly 34. More preferably, angle θ is about 106°. The width of dissecting tip 314 decreases from a proximal end of dissecting tip 314 to the distal end of dissecting tip 314. The width at the proximal end of dissecting tip 314 is approximately equal to the width of cartridge assembly 36. As discussed above, the dimensions and positioning of dissecting tip 314 on stapling device 10 permit positioning of stapling device 10 through a trocar cannula assembly sized to allow passage stapling device 10.

Distal tip 314d of dissecting tip 314 is preferably positioned proximally of the distal end of cartridge assembly 36. Alternately, distal tip 314d may be positioned adjacent to or distally of the distal end of cartridge assembly 36.

Dissecting tip 314 includes a substantially hollow recess 314e (FIG. 8f) which is configured to receive the distal end of anvil assembly 34. Dissecting tip 314 may be positioned over the distal end of anvil assembly 34 and secured thereto using any known fastening technique, e.g., adhesives, welding, friction fit, pins, screws, etc. Dissecting tip 314 is preferably formed from surgical grade metals or plastics although other known materials of construction are envisioned. Dissecting tip 314 functions basically in the same manner as discussed above with respect to dissecting tip 14 and will not be discussed in further detail herein.

Figure 9:
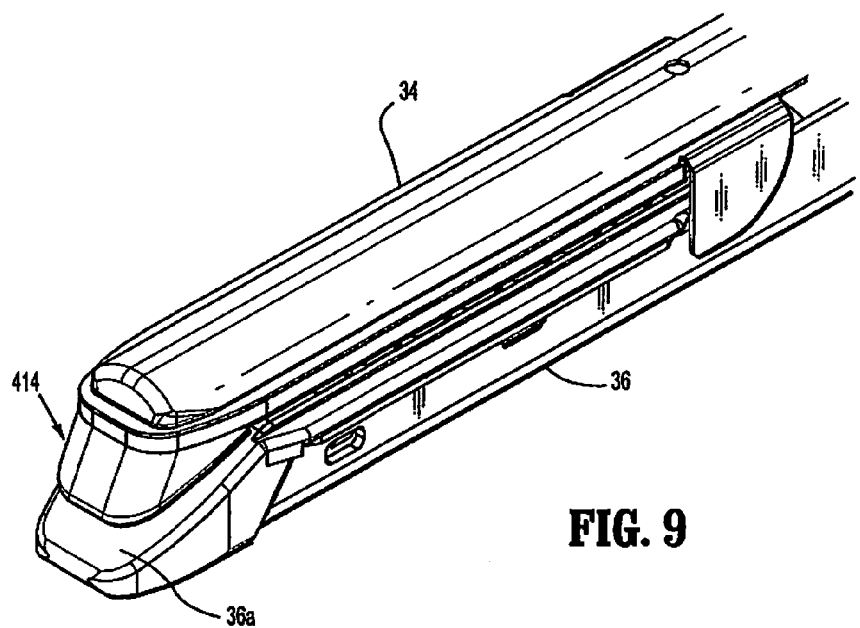
FIG. 9 is an enlarged top side perspective view from the front of the end effector of a surgical stapling device including another preferred embodiment of the presently disclosed dissecting tip.
Figure 9A:
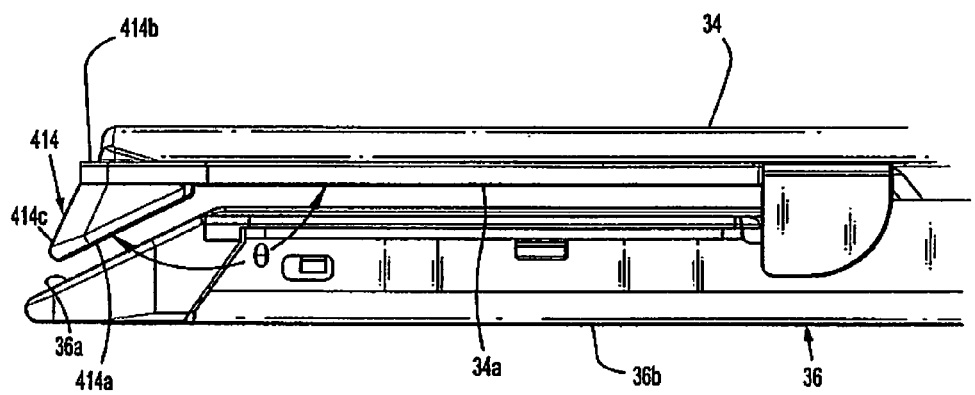
FIG. 9a is a side view of the dissecting tip and end effector shown in FIG. 9.
Figure 9B:
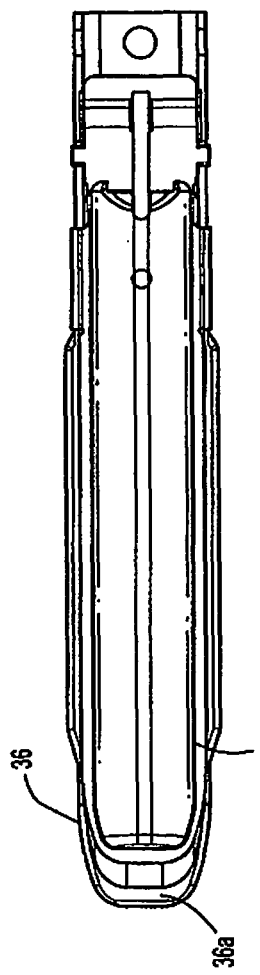
FIG. 9b is a top view of the dissecting tip and end effector of the surgical stapling device shown in FIG. 9.
Figure 9C:
FIG. 9c is a bottom view of the dissecting tip and end effector shown in FIG. 9b.
Figure 9E:
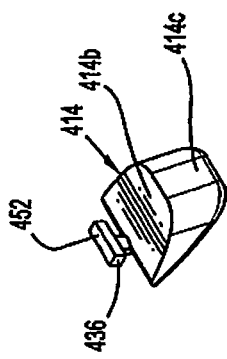
FIG. 9e is a side perspective view from the front of the presently disclosed dissecting tip shown in FIG. 9.
Figure 9D:
FIG. 9d is a front view of the dissecting tip and end effector shown in FIG. 9c.

FIGS. 9-9e illustrate another preferred embodiment of the presently disclosed dissecting tip shown generally as 414. Dissecting tip 414 is similar in shape to dissecting tip 314 but includes a peg extension 436 (FIG. 9e) to secure dissecting tip 414 to anvil assembly 34, rather than a hollow recess as will be further discussed below. Dissecting tip 414 includes an inner surface 414a, a top surface 414b, and a front surface 414c. Inner surface 414a preferably is substantially parallel to a tissue guide surface 36b on the distal end of cartridge assembly 36. Top surface 414b is flat and is positioned to abut against a distal surface of anvil assembly 34 which is contiguous with an inner tissue engaging surface 34a of anvil assembly 34. Front surface 414c is angled downwardly towards cartridge assembly 36 and preferably defines an angle θ (FIG. 9a) of between about 95° and about 135°. More preferably, angle θ is about 154°.

Peg extension 436 is a T-shaped member which extends upwardly from a proximal end of top surface 414b of dissecting tip 414. The upper portion 452 of T-shaped member 436 extends transversely across anvil assembly 34 and is dimensioned to be received in a linear slot (not shown) formed in the distal end of anvil assembly 34. To attach dissecting tip 414 to anvil assembly 34, upper portion 452 of T-shaped member 436 is positioned within the distal linear slots of anvil assembly 34 and dissecting tip 414 is rotated 90° to lock upper portion 452 within the linear slot and lock dissecting tip to anvil assembly 34. Additional fastening techniques may be used to fixedly secure dissecting tip 414 to anvil assembly 34, e.g., adhesives, welding, etc.

Figure 10:
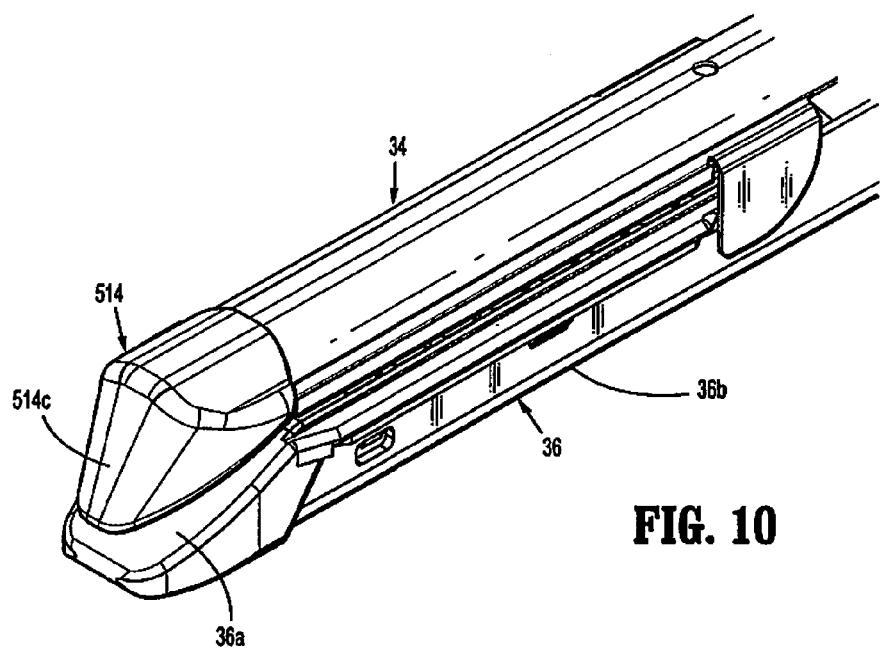
FIG. 10 is an enlarged side perspective view from the front of the end effector of a surgical stapling device including another preferred embodiment of the presently disclosed dissecting tip.
Figure 10A:
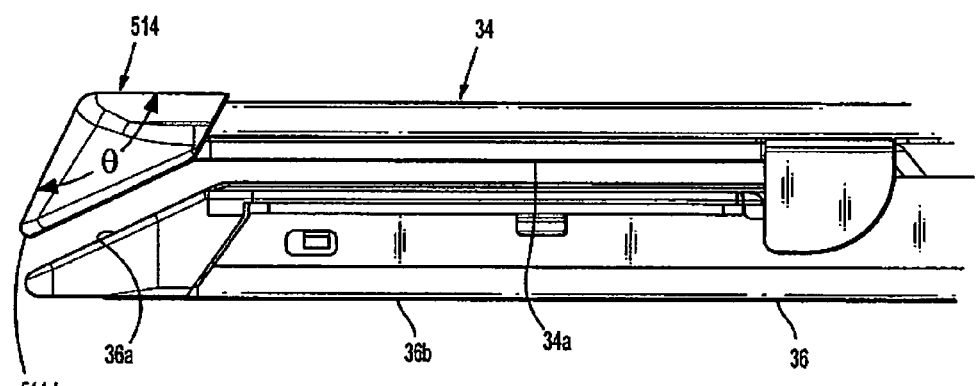
FIG. 10a is a side view of the dissecting tip and end effector shown in FIG. 10.

FIGS. 10-10e illustrate another preferred embodiment of the presently disclosed dissecting tip shown generally as 514. Dissecting tip 514 is substantially similar to dissecting tip 314 in construction but differs in that a distal tip 514d of dissecting tip 514 is narrower than and positioned above, over or adjacent to the distal end of cartridge assembly 36. Further, front surface 514c which preferably defines an angle θ (FIG. 10a) of between about 95° and about 135° is preferably about 115°. As discussed above with respect to dissecting tip 314, dissecting tip 514 defines a hollow recess (not shown) dimensioned and configured to receive the distal end of anvil assembly 34.

Figure 11:
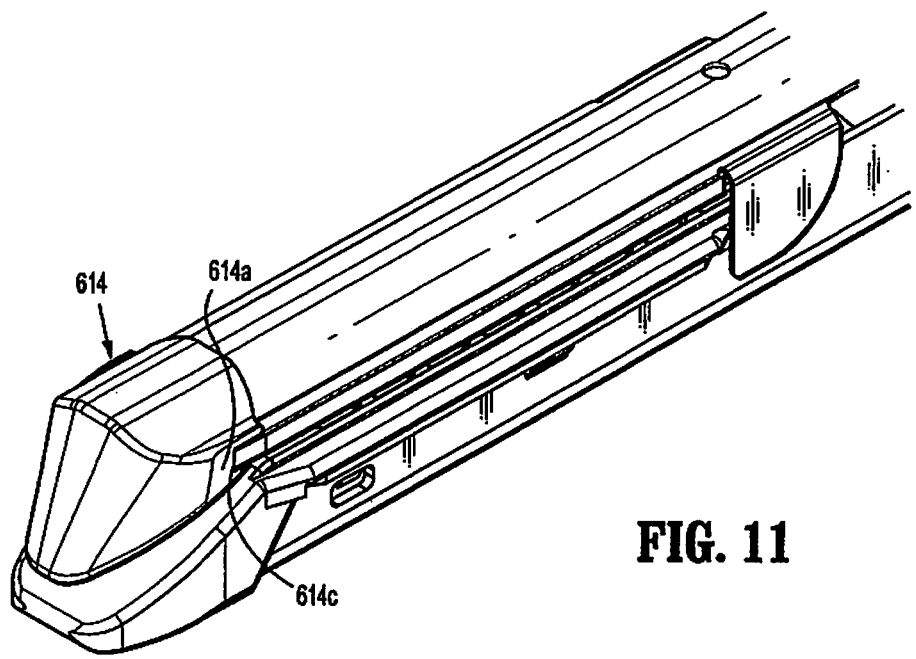
FIG. 11 is an enlarged side perspective view from the front of the end effector of a surgical stapling device including another preferred embodiment of the presently disclosed dissecting tip.
Figure 11A:
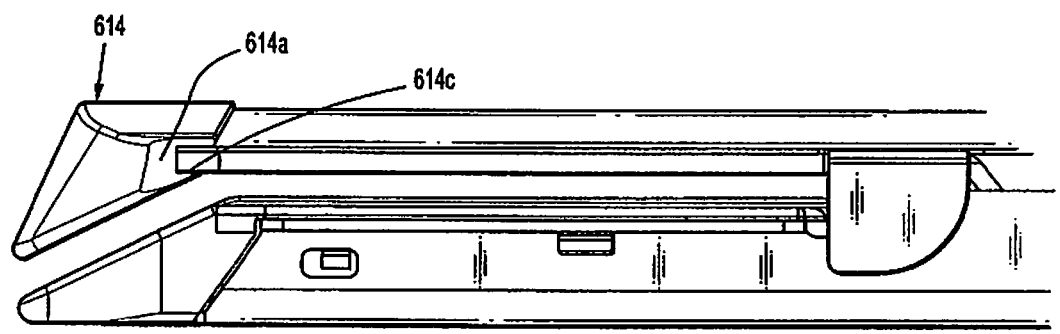
FIG. 11a is a side view of the dissecting tip and end effector shown in FIG. 11.

FIGS. 11-1e illustrate yet another preferred embodiment of the presently disclosed dissecting tip shown generally as 614. Dissecting tip 614 is substantially similar to dissecting tip 514 with the exception that dissecting tip 614 includes a pair of cutouts 614c formed in opposite tapered sidewalls 614a and 614b thereof. The tapered sidewalls 614a and 614b and cutouts 614c provide a smooth transition from dissecting tip 614 to anvil assembly 34 to prevent snagging and pulling of tissue.

Figure 12:
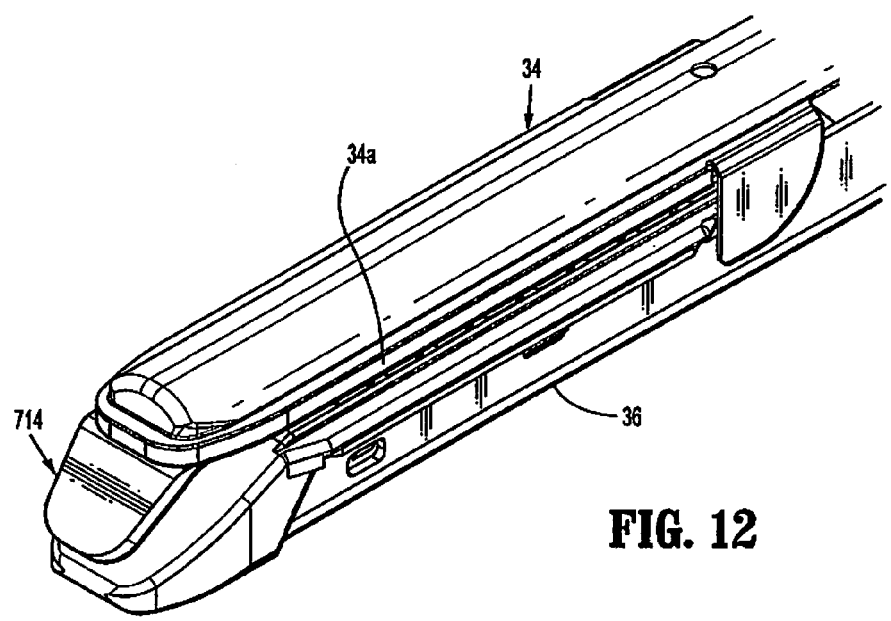
FIG. 12 is an enlarged side top perspective view from the front of the end effector of a surgical stapling device including another preferred embodiment of the presently disclosed dissecting tip.
Figure 12A:
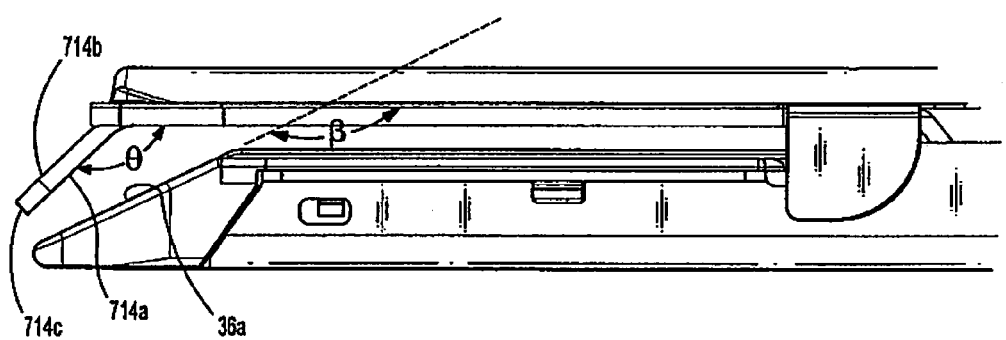
FIG. 12a is a side view of the dissecting tip and end effector shown in FIG. 12.
Figure 12B:
FIG. 12b is a top view of the dissecting tip and end effector of the surgical stapling device shown in FIG. 12.
Figure 12C:
FIG. 12c is a bottom view of the dissecting tip and end effector shown in FIG. 12b.
Figure 12E:
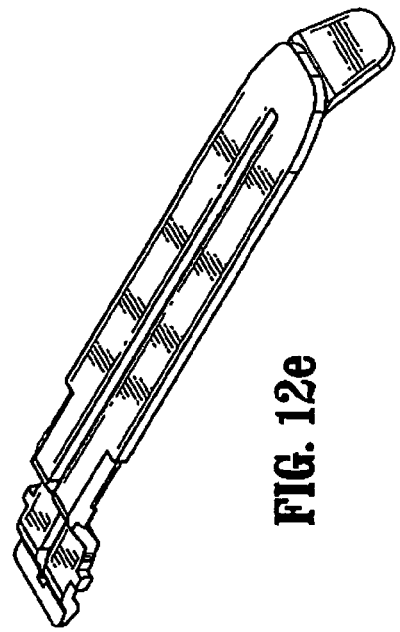
FIG. 12e is a side perspective view from the front of the presently disclosed dissecting tip shown in FIG. 12.
Figure 12D:
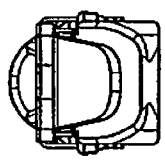
FIG. 12d is a front view of the dissecting tip and end effector shown in FIG. 12c.

FIG. 12-12e illustrate another preferred embodiment of the presently disclosed dissecting tip shown generally as 714. Dissecting tip 714 is formed integrally and/or monolithically with an anvil plate 34a (FIG. 12e) of anvil assembly 34 and is therefore preferably formed from a surgical grade metal. Dissecting tip 714 includes an inner surface 714a, an outer surface 714b and a distal tip 714c which preferably is rounded.

Inner and outer surfaces 714a and 714b are substantially flat and define an angle θ of preferably between about 105° and about 155° in relation to a longitudinal axis of anvil assembly 34. More preferably θ in about 136° Dissecting tip 714 extends downwardly towards cartridge assembly 36, at angle θ which is preferably less than an angle B defined between tissue guide surface 36a formed on the distal end of cartridge assembly 36 and a longitudinal axis of cartridge assembly 36. Although the invention of this disclosure can be employed on any sized SULU or end effector, for some applications shorter end effectors may be preferred.

It is preferred that the junction, blend or transition of the proximal portion of the inner surface of dissecting tip 14 with the plane of tissue contacting surface 34 of the anvil assembly be axially distal of the junction, blend or transition of tissue guide surface 36a and the tissue contacting surface of cartridge assembly 36. This provides space to allow tissue to be squeezed distally of the staple working portions of the tissue contacting surfaces of anvil assembly 34 and cartridge assembly 36 and helps maintain the desired tissue gap between those surfaces, during approximation and clamping. The configuration of dissecting tip 714 of end effector 12 shown in FIG. 12a exemplifies this preferred junctional relationship.

Figure 13:
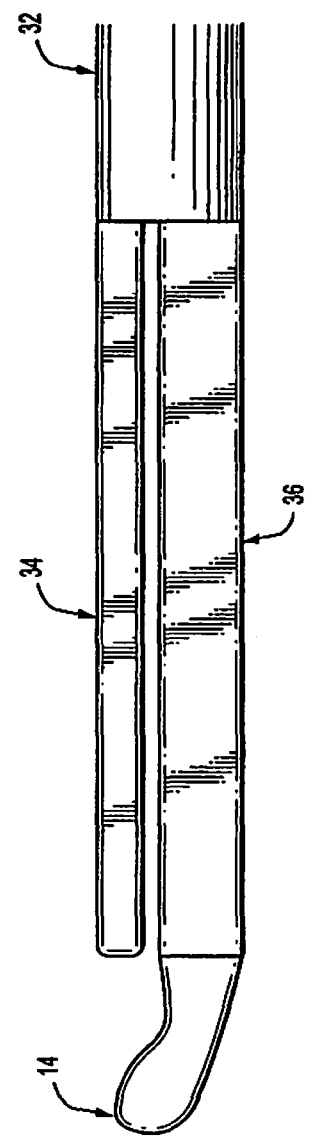
FIG. 13 is a schematic diagram of a surgical stapling device including an embodiment of the presently disclosed dissecting tip extending from a cartridge assembly thereof.

It will be understood that various modifications may be made to the embodiments disclosed herein. For example, the dissecting tip may be secured to other parts of the end effector including the cartridge assembly (FIG. 13). Further, each of the dissecting tips may be monolithically or integrally formed with the end effector, e.g., anvil assembly or cartridge assembly. Moreover, the angles and/or curves of the dissecting tip surface(s) may be modified to better suit a particular surgical procedure. Therefore, the above description should not be construed as limiting, but merely as exemplifications of preferred embodiments. Those skilled in the art will envision other modifications within the scope and spirit of the claims appended hereto.

What is claimed is:

1. A surgical stapling device comprising:
an elongated body portion;
an end effector including an anvil assembly movably supported in relation to a cartridge assembly between an open position and a clamped position, the cartridge assembly having a plurality of staples supported therein;
a dissecting tip extending distally from a distal end of the cartridge assembly and towards the anvil assembly in the distal direction, the dissecting tip having a blunt distal end configured to separate target tissue from certain tissue.

2. A surgical stapling device according to claim 1, wherein the dissecting tip includes smoothly curved inner and outer surfaces.

3. A surgical stapling device according to claim 2, wherein the distal end of the dissecting tip extends distally beyond the distal end of the anvil assembly.

4. A surgical stapling device according to claim 3, wherein the curved inner surface is formed by plural curved radii.

5. A surgical stapling device according to claim 4, wherein the width of the dissecting tip decreases from the proximal end of the dissecting tip to the distal end of the dissecting tip.

6. A surgical stapling device according to claim 5, wherein the dissecting tip is monolithically formed with the cartridge assembly.

7. A surgical stapling device according to claim 5, wherein the dissecting tip is secured to the cartridge assembly using a mechanical fastening technique.

8. A surgical stapling device according to claim 1, wherein the curved inner surface of the dissecting tip is contiguous with an inner tissue contact surface of the cartridge assembly.

9. A surgical stapling device according to claim 1, wherein the dissecting tip does not extend below a plane defined by an outer surface of the anvil assembly.

10. A surgical stapling device according to claim 1, wherein the anvil assembly includes a tissue contacting surface and an outer surface opposite the tissue contacting surface, the dissecting tip terminating between a plane defined by the tissue contacting surface of the anvil assembly and a plane defined by the outer surface of the anvil assembly when the end effector is in the clamped position.

11. A surgical stapling device according to claim 1, wherein the elongated body portion, the end effector and the dissecting tip are configured to be received through an access port.

12. A surgical stapling device comprising:
an elongated body portion;
an end effector including an anvil assembly movably supported in relation to a cartridge assembly between an open position and a clamped position, the anvil assembly including a tissue contacting surface and an outer surface opposite the tissue contacting surface;
a dissecting tip extending distally from a distal end of the cartridge assembly and towards the anvil assembly in the distal direction, wherein the dissecting tip terminates between a plane defined by the tissue contacting surface of the anvil assembly and a plane defined by the outer surface of the anvil assembly when the end effector is in the clamped position.

* * * * *